United States Patent
Bottlang et al.

(10) Patent No.: US 8,398,690 B2
(45) Date of Patent: Mar. 19, 2013

(54) ROTATIONALLY ASYMMETRIC BONE SCREW

(75) Inventors: Michael Bottlang, Portland, OR (US); Mark B. Sommers, Beaverton, OR (US)

(73) Assignee: Apex Biomedical Company, LLC, Portland, OR (US)

( * ) Notice: Subject to any disclaimer, the term of this patent is extended or adjusted under 35 U.S.C. 154(b) by 951 days.

(21) Appl. No.: 11/672,300

(22) Filed: Feb. 7, 2007

(65) Prior Publication Data
US 2008/0188899 A1   Aug. 7, 2008

(51) Int. Cl.
*A61B 17/56* (2006.01)
(52) U.S. Cl. .................. 606/308; 606/286
(58) Field of Classification Search .......... 606/60, 606/61, 67, 300–331, 68; 411/378–426
See application file for complete search history.

(56) References Cited

U.S. PATENT DOCUMENTS

| | | | |
|---|---|---|---|
| 2,654,284 A * | 10/1953 | Schevenell | 411/387.4 |
| 3,670,724 A | 6/1972 | Bosacco | |
| 4,959,064 A * | 9/1990 | Engelhardt | 606/65 |
| 4,978,350 A | 12/1990 | Wagenknecht | |
| 5,015,134 A * | 5/1991 | Gotoh | 411/386 |
| 5,046,905 A * | 9/1991 | Piacenti et al. | 411/387.2 |
| 5,053,036 A | 10/1991 | Perren et al. | |
| 5,382,195 A * | 1/1995 | Hiler | 470/9 |
| 5,709,686 A | 1/1998 | Talos et al. | |
| 5,725,581 A * | 3/1998 | Br.ang.nemark | 606/304 |
| 5,741,258 A | 4/1998 | Kkaue et al. | |
| 5,954,722 A | 9/1999 | Bono | |
| 6,129,730 A | 10/2000 | Bono et al. | |
| 6,238,417 B1 | 5/2001 | Cole | |
| 6,270,499 B1 | 8/2001 | Leu et al. | |
| 6,306,140 B1 | 10/2001 | Siddiqui | |
| 6,309,393 B1 | 10/2001 | Tepic et al. | |
| 6,558,387 B2 | 5/2003 | Errico | |
| 6,595,993 B2 | 7/2003 | Donno et al. | |
| 6,712,820 B2 | 3/2004 | Orbay | |
| 7,294,130 B2 | 11/2007 | Orbay | |
| 7,637,928 B2 | 12/2009 | Fernandez | |
| 7,695,472 B2 | 4/2010 | Young | |
| 8,137,042 B2 * | 3/2012 | Severns | 411/387.1 |

(Continued)

FOREIGN PATENT DOCUMENTS

| | | |
|---|---|---|
| EP | 0 355 035 B1 | 5/1994 |
| FR | 742.618 | 1/1933 |

(Continued)

OTHER PUBLICATIONS

PCT International Search Report issued for PCT/US2007/085753, Jul. 11, 2008, 4 pages.

*Primary Examiner* — Kevin T Truong
*Assistant Examiner* — Christopher Beccia
(74) *Attorney, Agent, or Firm* — Schwabe, Williamson & Wyatt

(57) ABSTRACT

Embodiments of the present invention provide rotationally asymmetric bone screws. Embodiments of the present invention provide mechanisms that reduce the bending stiffness of conventional shaft bone screws in order to yield a less-rigid fixation construct. Such a less-rigid construct enables a controlled amount of motion at a fracture site which in turn promotes bone healing. As a means to reduce the bending stiffness of positive-locking bone screws, embodiments of the present invention provide a bone screw having a non-circular cross-section over parts of the screw length and/or longitudinal slots along at least a portion of the bone screw.

11 Claims, 6 Drawing Sheets

U.S. PATENT DOCUMENTS

| | | | |
|---|---|---|---|
| 2002/0142265 A1* | 10/2002 | Weissman | 433/173 |
| 2002/0156474 A1 | 10/2002 | Wack et al. | |
| 2002/0198527 A1* | 12/2002 | Muckter | 606/73 |
| 2004/0047712 A1* | 3/2004 | Hofschneider | 411/396 |
| 2004/0071527 A1* | 4/2004 | Dendo | 411/508 |
| 2004/0172030 A1 | 9/2004 | Tipirrneni | |
| 2004/0230195 A1* | 11/2004 | Kaikkonen et al. | 606/72 |
| 2005/0010224 A1 | 1/2005 | Watkins et al. | |
| 2005/0010226 A1 | 1/2005 | Grady et al. | |
| 2005/0085818 A1 | 4/2005 | Huebner | |
| 2005/0101961 A1* | 5/2005 | Huebner et al. | 606/72 |
| 2005/0154390 A1 | 7/2005 | Biedermann | |
| 2005/0171544 A1* | 8/2005 | Falkner | 606/69 |
| 2005/0216005 A1* | 9/2005 | Howland | 606/61 |
| 2005/0240190 A1 | 10/2005 | Gall et al. | |
| 2005/0266383 A1* | 12/2005 | Aravena et al. | 433/173 |
| 2005/0277940 A1* | 12/2005 | Neff | 606/73 |
| 2006/0004361 A1 | 1/2006 | Hayeck et al. | |
| 2006/0116678 A1 | 6/2006 | Impellizzeri | |
| 2006/0129147 A1* | 6/2006 | Biedermann et al. | 606/61 |
| 2006/0173462 A1 | 8/2006 | Kay et al. | |
| 2006/0195099 A1* | 8/2006 | Bottlang | 606/67 |
| 2007/0016200 A1* | 1/2007 | Jackson | 606/61 |
| 2007/0160440 A1* | 7/2007 | Langewiesche | 411/386 |
| 2007/0183865 A1* | 8/2007 | Severns | 411/387.1 |
| 2007/0233071 A1* | 10/2007 | Dewey et al. | 606/61 |
| 2008/0140076 A1* | 6/2008 | Jackson | 606/60 |
| 2009/0062868 A1* | 3/2009 | Casutt | 606/316 |
| 2009/0171403 A1 | 7/2009 | Tipirneni | |

FOREIGN PATENT DOCUMENTS

| | | |
|---|---|---|
| JP | 2002-520114 A | 7/2002 |
| WO | WO 89/04150 | 5/1989 |
| WO | 2004112587 A | 12/2004 |

* cited by examiner

ROTATIONALLY ASYMMETRIC BONE SCREW

TECHNICAL FIELD

Embodiments of the present invention relate to the field of medical devices, and, more specifically, to a bone screw with features and/or attributes to provide positive-locking but flexible engagement to a bone.

BACKGROUND

Bone screws have typically been used to directly compress osteosynthesis plates onto a bone in order to align and stabilize a bone fracture. In this utilization, bone screws are not fixed rigidly to the bone plate, and the resulting frictional force between the plate and the bone is solely responsible for the stability of the osteosynthesis construct. Loosening of the screws in the bone or a resorption of the bone may thus easily lead to a loss of stability.

To avoid such loosening, and for the purpose of improving vascularity in a manner that minimizes damage to the bone surface, means for rigid locking of bone screws in a bone plate and elevated fixation of a bone plate over the bone surface have been introduced. For example, in one prior implementation, a positive-locking system between the screw and plate is effectuated by means of a bone plate with conical plate holes. The conical plate holes provide a rigid connection between the plate and the fixation screws, even after the screw-bone interface has loosened. In another prior implementation, a positive-locking system is effectuated by fitting screw holes in the plate with inside threads. These threaded holes accept bone screws fitted with a second threaded portion which is widened compared to the conventional threaded screw shank segment, to facilitate engagement with the inside thread of the plate hole. These positive-locking screws are designed to be threaded into the first bone surface underlying the plate, or into both the first and second bone surface of a quasi-cylindrical bone cross-section underlying the plate.

While these positive-locking osteosynthesis constructs provide superior stability, their stiffness may pose increased stress to the screw-bone interface. This has introduced failure modes, in which the bone resorbs or fractures adjacent to the outermost screw in the plate, since this screw absorbs the majority of the stress as the load is transferred from the bone to the plate.

Furthermore, the stiffness of the fixation construct suppresses small motion at the fracture site, which otherwise may be beneficial for fracture healing by inducing a fracture callus. Less stiff external fixators similarly impose positive-locking between bone pins and an external fixation bar. Flexion of the considerably long fixation pins allows for controlled motion at the fracture site that may be of sufficient magnitude to induce fracture healing by callus formation. While positive-locking plate-screw constructs employ a similar fixation principle as an external fixator, the close proximity of the plate to the bone surface prohibits elastic flexion of the screw segment between the plate and the bone.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

DETAILED DESCRIPTION OF EMBODIMENTS OF THE INVENTION

Figure 1:
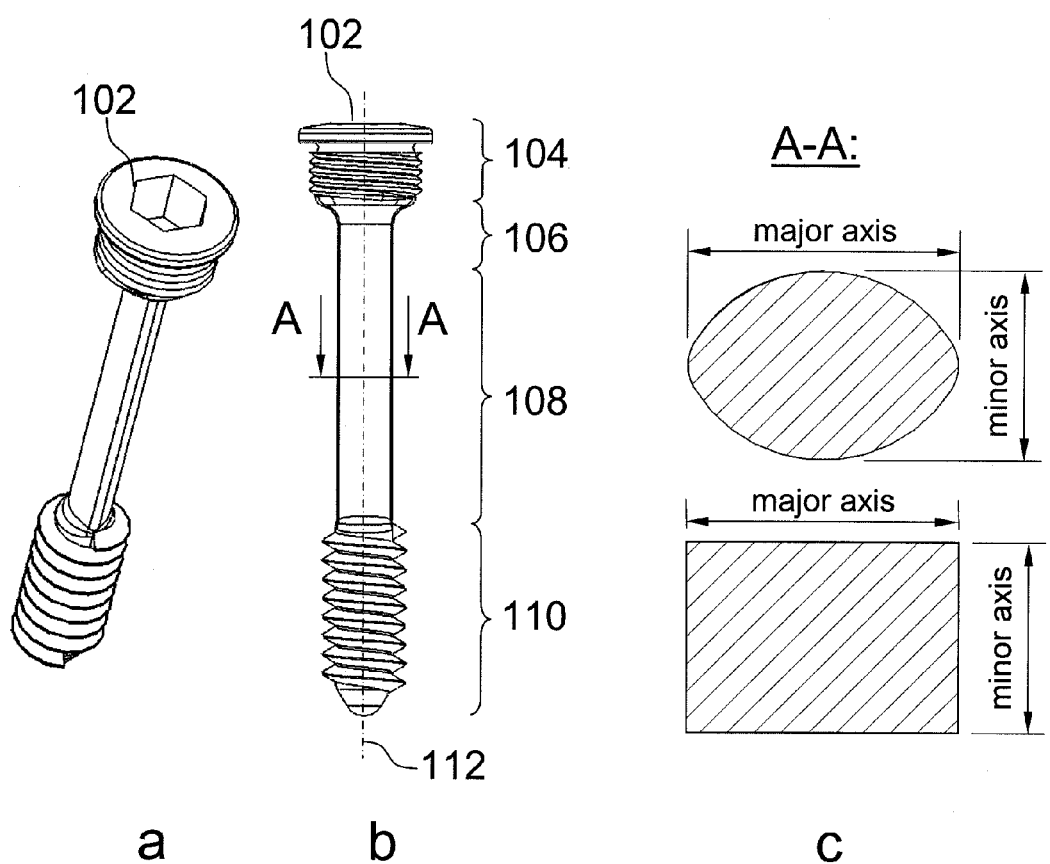
FIGS. 1a, 1b, and 1c illustrate a bone screw in accordance with various embodiments of the present invention.

In the following detailed description, reference is made to the accompanying drawings which form a part hereof, and in which is shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" means A or B. For the purposes of the description, a phrase in the form "A and/or B" means "(A), (B), or (A and B)". For the purposes of the description, a phrase in the form "at least one of A, B, and C" means "(A), (B), (C), (A and B), (A and C), (B and C), or (A, B and C)". For the purposes of the description, a phrase in the form "(A)B" means "(B) or (AB)" that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

In various embodiments of the present invention, methods, apparatuses, and systems for positive-locking but flexible engagement to bone are provided. Embodiments of the present invention provide a bone screw, an osteosynthesis construct, and associated methods for using the bone screw and/or the osteosynthesis construct.

Rotationally symmetric approaches for positive-locking but flexible engagement to bone have been provided, for example, in U.S. patent application Publication No. 2006/0195099, filed Feb. 15, 2005, the entire contents of which are hereby incorporated by reference. Embodiments of the present invention alternatively provide rotationally asymmetric bone screws.

Embodiments of the present invention provide mechanisms that reduce the bending stiffness of conventional shaft bone screws in order to yield a less-rigid fixation construct. Such a less-rigid construct enables a controlled amount of motion at a fracture site which in turn promotes bone healing. As a means to reduce the bending stiffness of positive-locking bone screws, in an embodiment, a bone screw having a non-circular cross-section over parts of the screw length may be utilized. Bending such a bone screw in the direction of its smallest cross-sectional axis yields a lower bending stiffness as compared to bending the screw in the direction of its largest cross-sectional axis. Thus, the term "rotationally asymmetric" may be used to describe such screws as the bending stiffness may differ depending on the direction of the force/load applied to the bone screw. In an embodiment, a low bending stiffness around the smallest cross-sectional axis may be desirable to achieve a fixation construct support that is less stiff under distinct loading directions. In an embodiment, a large cross-sectional axis provides adequate shear strength of the bone screw. Thus, in combination in an embodiment, a bone screw having different cross-sectional axes may take advantage of low stiffness and higher flexibility in one or more directions, and higher stiffness and strength in one or more other directions.

In an embodiment, as an alternative mechanism to reduce bending stiffness of positive-locking bone screws, one or more slots may be introduced in the screw shaft in a substantially longitudinal direction. In an embodiment, depending on the slot arrangement, the slots may be used to control the direction-dependent bending stiffness of the bone screw.

In an embodiment, in order to obtain plate and screw fixation constructs with a low/reduced stiffness under axial loading, the bone screws may be locked to the fracture plate in a manner that screw bending under axial loading occurs in direction of their lowest bending stiffness. Such a feature may be achieved by machining the threads of the screw head as well as the threads in the corresponding plate hole in a rotationally defined "timed" manner. Timing the screw threads with the threads of the plate ensures that upon full insertion of the screws in the plate, each screw has the desired rotational alignment and thus the desired preferential bending direction.

In an embodiment, whether or not using timed screw threads, screw heads and/or fracture plates may be provided with additional alignment mechanisms. For example, in an embodiment, a proper orientation of a screw in a fracture plate may bring into alignment a line on the screw head with a line on the fracture plate.

In various embodiments, bone screws may be made of a variety of suitable materials, such as a biocompatible material, for example stainless steel or titanium.

FIGS. 1a, 1b, and 1c illustrate a bone screw in accordance with an embodiment of the present invention. In an embodiment, the bone screw includes a threaded head portion 104, having a head 102, and an adjoining shaft portion having a neck section 106, a mid section 108, and a threaded front end 110 (FIG. 1b). In an embodiment, head 102 may comprise a variety of screw drive types such as slotted, Phillips, hex, Robertson, Torx, etc. In an embodiment, the bone screw is a unitary piece having a central axis 112, whereby its geometry may or may not be rotationally symmetrical. For embodiments of the bone screw that are rotationally asymmetrical, mid section 108 and/or neck section 106 may have a non-circular cross section, such as an elliptical or rectangular cross section having a minor axis and a major axis (FIG. 1c). Consequently, the bending stiffness of the bone screw may depend on the direction in which a bending force is applied. In an embodiment, the lowest bending stiffness is obtained for bending of the screw shaft around its minor axis.

While FIG. 1, and other figures herein, illustrates a shaft that appears to have relatively uniform cross-sections, in embodiments, the cross-sections of the shafts of such bone screws may have relatively uniform cross-sections along the length of the shaft or may have cross-sections that vary along the length of the shaft. In an embodiment, a portion of a shaft of a bone screw may have a non-circular cross-section and another portion of the shaft may have a different non-circular cross-section or may have a circular cross-section. In such a bone screw, a suitable transition section provides the transition between or among the varied cross-sections.

In an embodiment, the threads of a threaded front end of a bone screw may extend at least partially along the mid section of the screw, whether the mid section is circular or non-circular in cross-section. In an embodiment in which a mid section has a non-circular cross-section, threads may be manufactured on all or a portion of the mid-section such that the threads maintain a circular cross-section. In such an embodiment, the core shape of the mid-section may comprise the non-circular cross-section and thus impart the direction-dependent bending stiffness, while the circular threads may allow for further engagement with the far cortex.

Figure 2:
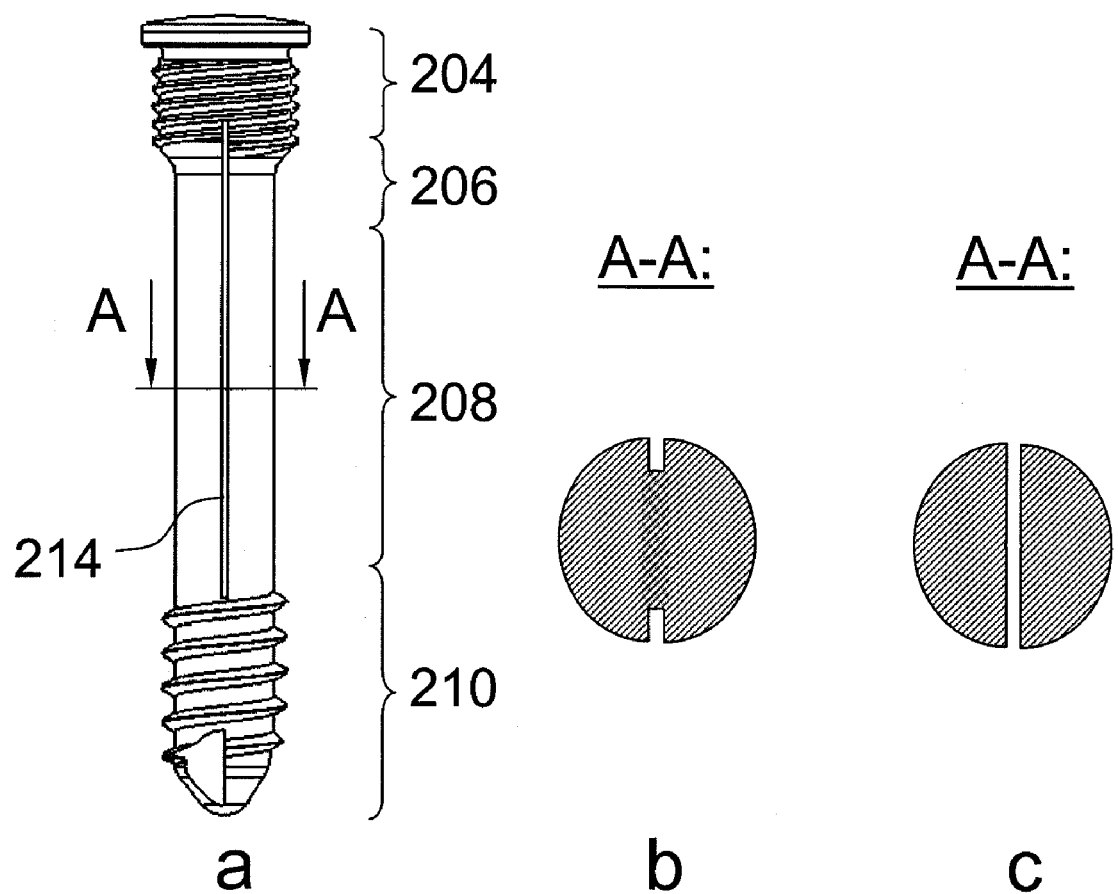
FIGS. 2a, 2b, and 2c illustrate a bone screw in accordance with various embodiments of the present invention.

FIGS. 2a, 2b, and 2c illustrate an embodiment of a bone screw. In an embodiment, as a means to reduce the bending stiffness of the bone screw, threaded head portion 204, neck section 206, mid section 208, and/or threaded front end 210 may have one or more longitudinal slots 214 (FIG. 2a). For purposes of the present invention, the term "longitudinal slot" refers to a slot in a screw shaft that is substantially longitudinal in orientation although it may or may not be parallel to the longitudinal axis of the screw. In embodiments, slot(s) 214 may laterally penetrate the screw shaft partially (FIG. 2b) or fully (FIG. 2c). In embodiments, the desired amount of bending stiffness may be achieved by selecting the appropriate slot depth, slot length, and slot configuration.

Figure 3:
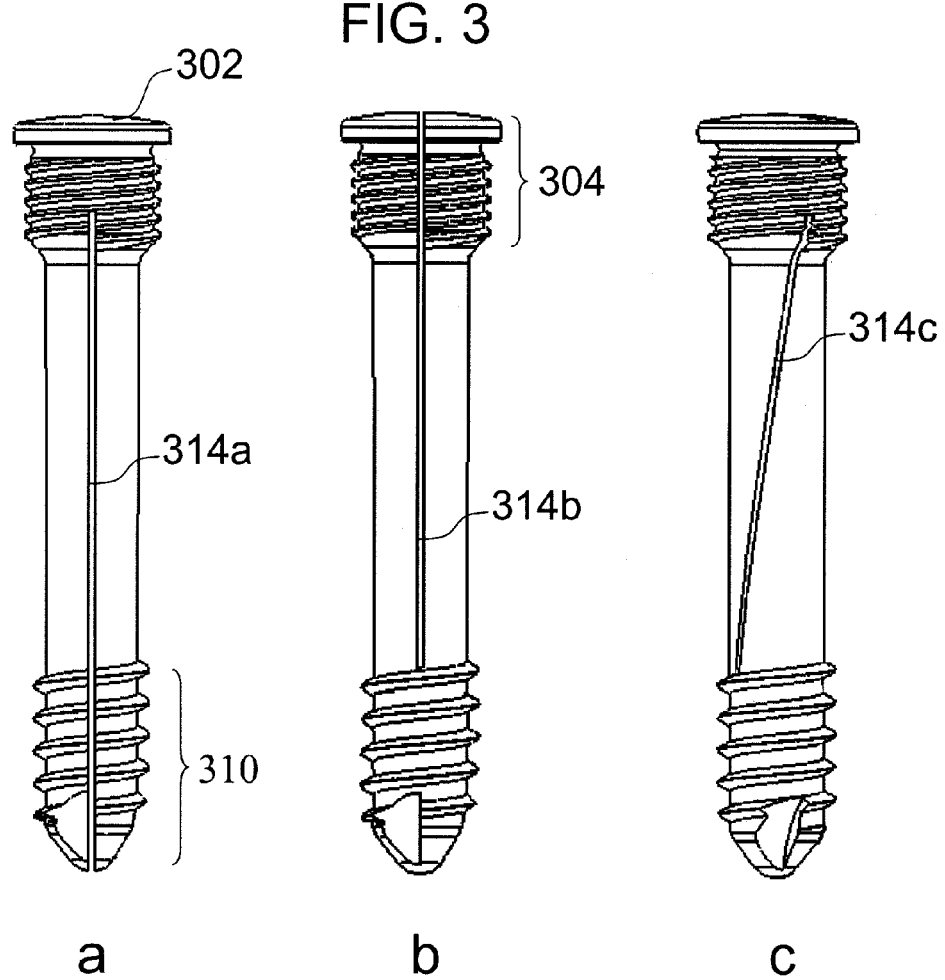
FIGS. 3a, 3b, and 3c illustrate various configurations of slotted bone screws in accordance with various embodiments of the present invention.

FIGS. 3a, 3b, and 3c illustrate various configurations of slots 314a, 314b, and 314c, whereby one or more partially or fully penetrating slots may extend into or through threaded front end 310 of the bone screw (FIG. 3a) or into or through head 302 of the bone screw (FIG. 3b). In embodiments, these screw configurations have a reduced bending stiffness as a result of the presence of the slot(s) even if the screw slot in threaded front end 310 or head 302 is compressed upon insertion of the screw into the far cortex, near cortex, or plate. Alternatively, in an embodiment, one or more partially or fully penetrating longitudinal slots 314c may be formed in a curved manner at least partially around the screw shaft to achieve a multi-directional reduction in bending stiffness (FIG. 3c).

Figure 4:
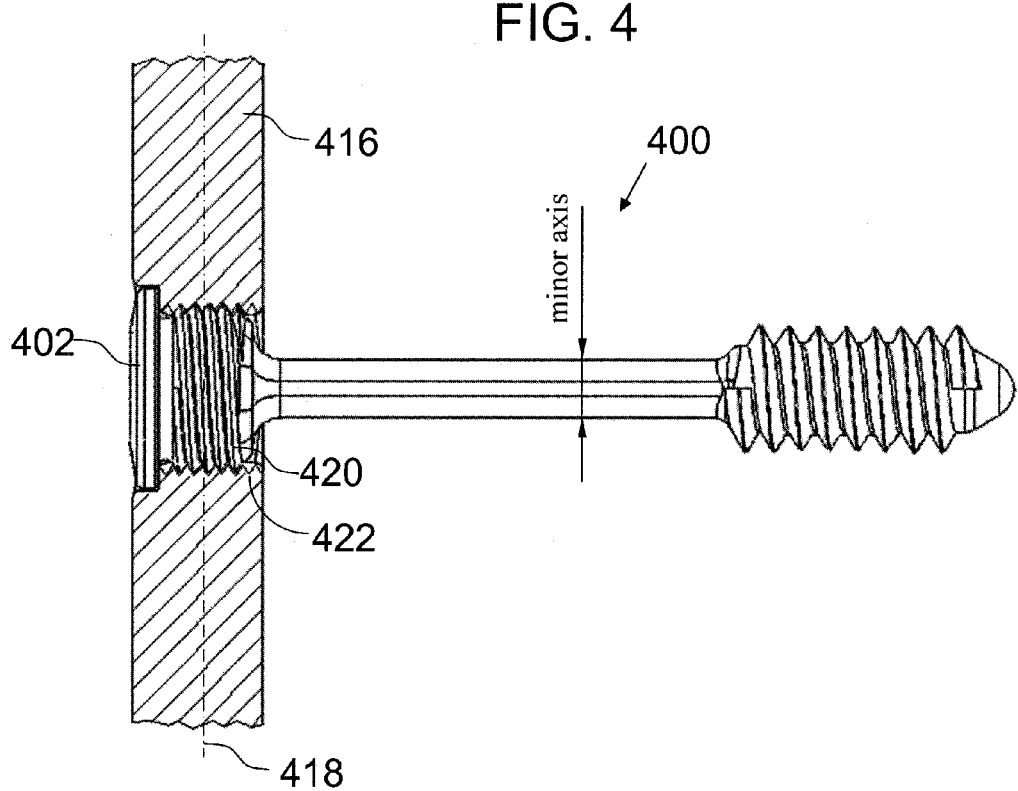
FIG. 4 illustrates a bone screw in association with a fracture plate in accordance with various embodiments of the present invention.

In an embodiment, FIG. 4 illustrates a bone screw 400 with a non-circular shaft cross-section in association with a fracture plate 416 for positive locking of screw head 402 to plate 416. In an embodiment, in a fully inserted position, the minor diameter of the screw shaft may be aligned with the longitudinal plate axis 418. In an embodiment, this rotational alignment may be achieved by manufacturing both the screw threads 420 and the plate hole threads 422 in a rotationally defined or timed manner.

Figure 5:
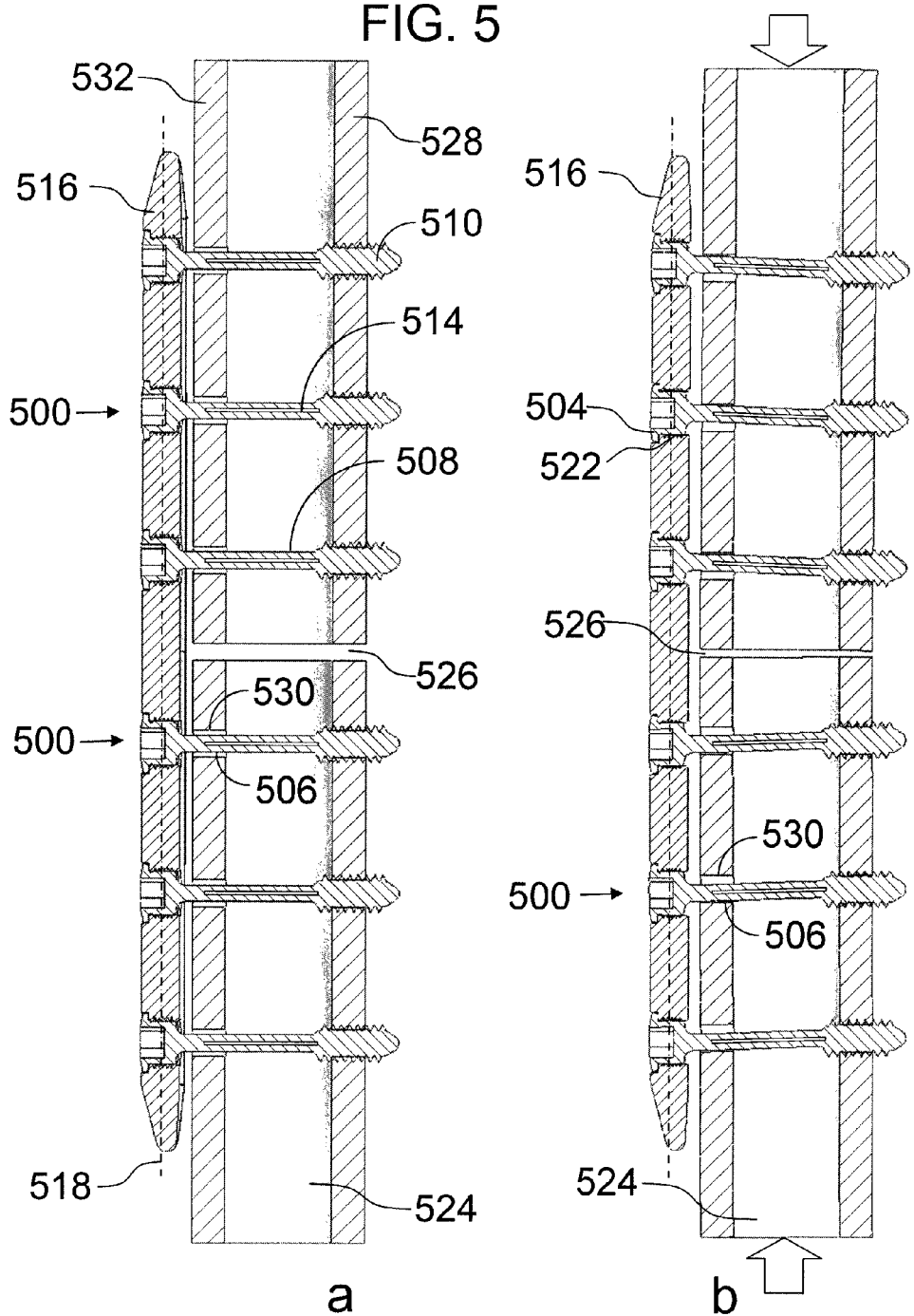
FIGS. 5a and 5b illustrate a series of bone screws in association with a fracture plate in accordance with various embodiments of the present invention.

FIGS. 5*a* and 5*b* illustrate six slotted bone screws 500 in association with a fracture plate 516, affixed to tubular bone 524 with a simulated fracture gap 526. Although in FIGS. 5*a* and 5*b* six screws are shown, any suitable number of screws may be utilized such as 2, 3, 4, 5, 6, or more, depending on the particular application. In an embodiment, bone screws 500 may be fixed to plate 516 in a timed manner in order to ensure that, when each bone screw 500 is fully inserted, each slot 514 is rotationally aligned perpendicular to the longitudinal plate axis 518. In an embodiment, threaded front end 510 of each screw may be fixed in far cortex 528, while an axial and translational degree of freedom remains between screw neck 506 and the corresponding hole 530 in near cortex 532. Upon axial loading of tubular bone 524, bone screws 500 may deform, preferentially in the direction of the lowest bending stiffness, thereby allowing for compressive displacement at fracture gap 526 (FIG. 5*b*). Aligning the lowest bending stiffness with the axial loading direction allows for suitable motion of the bone plate and bone screws to occur which aids in healing and avoids unacceptable strain on the bone.

In various embodiments, the flexibility of the bone screw may be sufficient to accommodate excessive loading of the osteosynthesis construct (screws and plate). In such event, the low bending stiffness provides for a controlled failure mechanism to delay or prevent more detrimental failure modes, such as plate bending or bone fracture. Further, in an embodiment, this elasticity may also improve the ability of screw head portion 504 to engage bone plate 516, especially for embodiments in which engagement involves engaging threads of screw head portion 504 with threaded through hole 522 of bone plate 516, and when the holes in the bone and threaded through hole 522 of bone plate 516 are not precisely concentric.

In embodiments, threaded front ends 510 may incorporate self-tapping features that allow for insertion of bone screws 500 without the need for tapping of a screw thread. Additionally, in embodiments, threaded front end(s) 510 may also incorporate a self-drilling feature, which allows for screw insertion without the need for pre-drilling a hole in the cortex. Still further, in embodiments, threaded front end(s) 510 may also incorporate a self-drilling feature located toward mid section 508, which allows for screw removal (withdrawal) to penetrate newly formed bone at the perimeter of screw hole (cavity) 530 in near cortex 532. Such features are illustrated in U.S. patent application Publication No. 2006/0195099, filed Feb. 15, 2005, the entire contents of which are hereby incorporated by reference.

In embodiments, mid section 508 may be provided with a short, elevated cutting flute having a diameter that is at least as big as the outer diameter of threaded front end(s) 510, and may be up to twice as big as the outer diameter of threaded front end(s) 510. Thus, during screw insertion, the cutting flute may further expand the diameter of screw hole 530 in near cortex 532, initially established with a smaller diameter for allowing threaded front end(s) 510 to pass through, to ensure that neck 506 of bone screw 500 is not rigidly fixed in near cortex 532. During screw removal/withdrawal, the cutting flute may again expand screw hole 530 in near cortex 532 to remove newly formed bone. Such features are illustrated in U.S. patent application Publication No. 2006/0195099, filed Feb. 15, 2005, the entire contents of which are hereby incorporated by reference.

In embodiments such as shown in FIGS. 5*a* and 5*b*, even though multiple screws may be utilized in a suitable osteosynthesis construct, the multiple screws need not be identical. In an embodiment, screws located close to the fracture site may have a bending stiffness different from those further away from the fracture site. In addition, in an embodiment, one or more screws of a set of screws in an osteosynthesis construct may be rotationally asymmetric and others may be rotationally symmetric. In addition, one or more screws of a set of screws in an osteosynthesis construct may be conventional uni-cortical screws or positive-locking screws that engage in both the near and far cortex (bi-cortical screws).

In an embodiment, a far-cortical locking screw may be used at one or both ends of a bone plate, while the remaining screws may be conventional bi-cortical and/or uni-cortical locking screws. Since, in embodiment, the load may be highest at the ends of the bone plate, use of an FCL screw at one or both ends of the plate may prevent bone fractures through the outermost screw holes.

While the foregoing descriptions have been presented with bone screws illustrated in use with a tubular bone, those skilled in the art will appreciate that the present invention is not so limited, and may be practiced with non-tubular bones as well.

Figure 6:
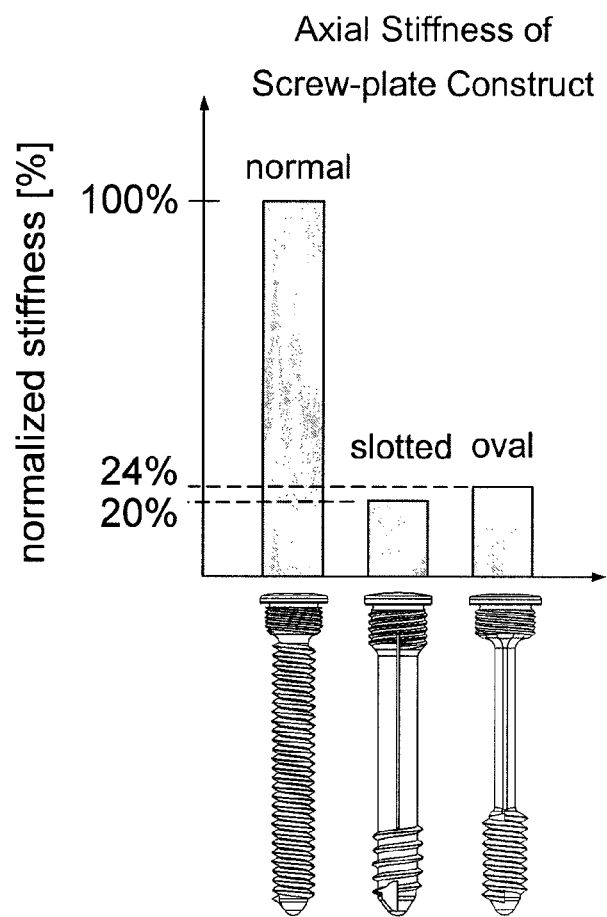
FIG. 6 illustrates the relative axial stiffness of bone screws in accordance with various embodiments of the present invention in comparison with conventional bone screws.

FIG. 6 illustrates the axial stiffness of screw and plate constructs, whereby the use of slotted or non-circular cross-section screws reduced the construct stiffness to 24% and 20%, respectively, relative to conventional (normal) screws. These results were obtained from computational modeling of screw and plate constructs using Finite Element Analysis, which quantifies the load deformation behavior of mechanical structures.

Thus, in embodiments, it may be seen from the foregoing that the timed application of positive locking rotationally asymmetric bone screws, and methods for using them, may provide one or more advantages. In an embodiment, rotationally asymmetric bone screws reduce axial stiffness of a fixation construct to promote fracture healing by enabling compression at the fracture gap. In an embodiment, rotationally asymmetric bone screws retain a higher shear strength compared to far cortical locking screws incorporating a rotationally symmetric reduction of the screw shaft diameter. In an embodiment, rotationally asymmetric bone screws yield fixation constructs that provide constructs of higher torsional stiffness compared to far cortical locking screws with a rotationally symmetric reduction of the screw shaft diameter. In an embodiment, rotationally asymmetric bone screws may yield a larger contact interface between the screw shaft and the near cortex of tubular bone upon screw shaft bending in far cortical locking applications.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. An osteosynthesis construct, comprising:
   a bone plate having two or more holes with locking threads for fixation of bone screws to the plate; and two or more bone screws for positive-locking engagement with the plate, at least one of said two or more bone screws comprising
a shaft having a neck section, a mid section, and a threaded front end, at least one of said neck section and said mid section being rotationally asymmetric to impart to the bone screw a direction-dependent bending stiffness having a preferential direction of bending having a lower bending stiffness compared to a bending stiffness in a direction perpendicular to the preferential direction of bending; and
a threaded head portion adjoining the shaft, said threaded head portion having threads to provide for a positive-locking engagement of the bone screw with the bone plate, wherein said threads of said threaded head portion are rotationally timed with said threads of said plate holes to provide for a positive locking engagement of the bone screw with the bone plate resulting in a predefined final orientation of the bone screw with respect to the plate to align the bone screw to exploit the preferential direction of bending.

2. The osteosynthesis construct of claim 1, wherein said rotationally asymmetric neck section and/or mid section comprises a non-circular cross-section.

3. The osteosynthesis construct of claim 2, wherein said non-circular cross-section comprises an oval cross-section.

4. The osteosynthesis construct of claim 2, wherein said non-circular cross-section comprises a rectangular cross-section.

5. The osteosynthesis construct of claim 1, wherein said rotationally asymmetric neck section and/or mid section comprises one or more longitudinal slots.

6. The osteosynthesis construct of claim 5, wherein at least one of said one or more longitudinal slots penetrates partially through at least a portion of said shaft and/or said threaded head portion.

7. The osteosynthesis construct of claim 5, wherein at least one of said one or more longitudinal slots penetrates fully through at least a portion of said shaft and/or said threaded head portion.

8. The osteosynthesis construct of claim 5, wherein at least one of said one or more longitudinal slots is curved.

9. The osteosynthesis construct of claim 1, wherein said predefined final orientation of the bone screw with respect to the plate aligns in parallel said preferential direction of bending with a longitudinal axis of the bone plate.

10. The osteosynthesis construct of claim 1, wherein said threaded front end is configured to secure said bone screw in a far cortex of a bone.

11. The osteosynthesis construct of claim 1, wherein at least one of said two or more bone screws comprises a bi-cortical or uni-cortical locking screw.

* * * * *